United States Patent [19]

Carter et al.

[11] Patent Number: 5,139,702
[45] Date of Patent: Aug. 18, 1992

[54] NAPHTHYLAMINE POLYCARBOXYLIC ACIDS

[75] Inventors: Charles G. Carter, Silver Spring; Robert P. Kreh, Jessup, both of Md.; Lai-Duien G. Fan, Lake Zurich, Ill.

[73] Assignee: W. R. Grace & Co.-Conn., New York, N.Y.

[21] Appl. No.: 782,360

[22] Filed: Oct. 24, 1991

[51] Int. Cl.$^5$ .................. C23F 11/12; C23F 11/14
[52] U.S. Cl. ...................... 252/392; 252/391; 252/389.61; 252/389.62; 252/394; 252/395; 252/396; 252/180; 210/698; 562/490; 562/488; 422/16; 422/17
[58] Field of Search ............... 562/490, 488; 210/698; 252/180, 389.61, 389.62, 391, 392, 394, 395, 396; 422/16, 17

[56] References Cited

U.S. PATENT DOCUMENTS

| | | | |
|---|---|---|---|
| 3,429,963 | 2/1969 | Shedlovsky | 424/86 |
| 3,776,850 | 12/1973 | Pearson et al. | 252/174.24 |
| 3,799,951 | 3/1974 | Guthrie et al. | 562/459 |
| 3,929,874 | 12/1975 | Beerman et al. | 562/462 |
| 4,627,977 | 12/1986 | Gaffar et al. | 424/52 |
| 4,654,159 | 3/1987 | Bush et al. | 424/259 |
| 4,661,341 | 4/1987 | Benedict et al. | 424/48 |
| 4,846,650 | 7/1989 | Benedict et al. | 424/55 |
| 4,971,724 | 11/1990 | Kalota et al. | 562/568 |

FOREIGN PATENT DOCUMENTS 2408591 9/1975 Fed. Rep. of Germany.
3739610 11/1987 Fed. Rep. of Germany.

OTHER PUBLICATIONS

Chemical Abstracts 81 77484r (1974), Y. Matsuzawa et al.
Chem. Soc. Jap. 40, 2977, J. Oh-hashi et al.
Chemical Abstracts 57, 16732g (1962) Hamptman et al.

Primary Examiner—Deborah L. Kyle
Assistant Examiner—Valerie Fee
Attorney, Agent, or Firm—James P. Barr

[57] ABSTRACT

A composition useful for treating aqueous systems comprising a naphthylamine polycarboxylic acid having the formula:

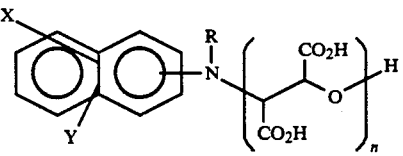

wherein X is $CO_2H$ or $SO_3H$, Y is H, $C_1$ to $C_6$ alkyl, $CO_2H$ or $SO_3H$, R is H, $C_1$ to $C_6$ alkyl, $CO_2R'$ or $COR'$, R' is $C_1$ to $C_6$ alkyl, n is an integer from 1 to 20, and water soluble salts thereof.

20 Claims, No Drawings

NAPHTHYLAMINE POLYCARBOXYLIC ACIDS

FIELD OF THE INVENTION

The present invention is directed to certain novel compositions which are useful in the field of water treatment, and more specifically to certain novel naphthylamine polycarboxylic acids and to a method of preventing the formation of scale on surfaces in contact with an aqueous system and/or a method of inhibiting corrosion of ferrous-based metals in contact with an aqueous system.

BACKGROUND OF THE INVENTION

Most industrial aqueous systems contain alkaline earth metal cations, such as calcium, magnesium, and the like, as well as numerous anions such as bicarbonate, carbonate, sulfate, and the like. When the concentration of the various combinations of cation and anions exceed the solubility of their reaction products, precipitates tend to form until the product solubility concentrations are no longer exceeded. As these reaction products precipitate on the surfaces of the aqueous systems, they form what is known as scale. The precipitation of calcium carbonate is by far the most common form of scale in industrial aqueous systems. This occurs when the ionic product of calcium and carbonate exceeds the solubility of the calcium carbonate and a solid phase of calcium carbonate forms.

The formation of scale in industrial aqueous systems represents a major problem since it reduces heat transfer efficiency on heat exchanger surfaces, increases corrosion problems and reduces flow of the water through the system. The addition of inorganic and, more recently, all organic polyphosphonates to these aqueous systems is known to inhibit scale formation. These compositions are generally added to the system in substoichiometric amounts to the scale forming salt and are known to those in the art as threshold inhibitors. Threshold inhibition describes the phenomenon whereby a sub-stoichiometric amount of a scale inhibitor can stabilize a solution from precipitation. Threshold inhibition generally takes place under conditions where a small amount, e.g. 1 ppm to 100 ppm of an additive, will stabilize the solution which contains many orders of magnitude greater concentration of scale forming salts.

Iron and iron-based metal-containing alloys, such as mild steel, are well-known materials used in constructing the apparatus of aqueous systems. In these systems water circulates, contacts the ferrous-based metal surface, and may be concentrated, such as by evaporation, of a portion of the water from the system. Even though such, metals are readily subject to corrosion in such environments, they are used over other metals due to their strength and availability.

It is known that various materials which are naturally or synthetically occurring in the aqueous systems, especially systems using water derived from natural resources such as seawater, rivers, lake and the like, attack ferrous-based metals. The term "ferrous-based metals", as used herein refers to any ferrous-containing metals. Typical devices in which the ferrous-based metal parts are subject to corrosion include evaporators, single and multi-pass heat exchangers, cooling towers, and associated equipment and the like. As the system water passes through or over the device, a portion of the system water evaporates causing a concentration of the dissolved materials contained in the system. These materials approach and reach a concentration at which they may cause severe pitting and corrosion which eventually requires replacement of the metal parts. Various corrosion inhibitors have been previously used.

Chromates and inorganic phosphates or polyphosphates have been used in the past to inhibit the corrosion of metals which is experienced when the metals are brought into contact with water. The chromates, though effective, are highly toxic and, consequently, present handling and disposal problems. Phosphates are nontoxic. However, due to the limited solubility of calcium phosphate, it is difficult to maintain adequate concentrations of phosphates in many instances. The polyphosphates are also relatively non-toxic, but tend to hydrolyze to form orthophosphate which in turn, like phosphate itself, can create scale and sludge problems in aqueous systems (e.g. by combining with calcium in the system to form calcium phosphate). Moreover, where there is concern over eutrophication of receiving waters, excess phosphate compounds can provide disposal problems as nutrient sources. Borates, nitrates and nitrites have also been used for corrosion inhibition. These too, can serve as nutrients in low concentrations, and/or represent potential health concerns at high concentrations.

In addition, environmental considerations have also recently increased concerns over the discharge of other metals, such as zinc, which previously were considered acceptable for water treatment.

Much recent research has been concerned with the development of organic scale and corrosion inhibitors which can reduce reliance on the traditional inorganic inhibitors. Among the organic inhibitors successfully employed are numerous organic phosphonates. These compounds may generally be used without detrimentally interfering with other conventional water treatment additives. There is a continuing need, however, for safe and effective water treatment agents which can be used to control corrosion.

Many of the organic scale inhibitors and corrosion inhibitors used in industrial aqueous systems (e.g. hydroxyethylidene diphosphonic acid) are themselves very sensitive to calcium hardness and prone to form deposits of their calcium salts. This limits the range of hardness in which such materials can be usefully applied as scale inhibitors or corrosion inhibitors. There is a continuing need for safe and effective water treating agents which can be used to control scale formation and to inhibit corrosion, particularly when substantial calcium carbonate is present in the system water.

SUMMARY OF THE INVENTION

It is an object of this invention to provide certain novel scale inhibiting compositions.

It is another object of this invention to provide certain novel corrosion inhibiting compositions.

It is another object of this invention to provide a method of treating aqueous systems to effectively inhibit or prevent the formation of scale deposits on surfaces in contact with the aqueous system.

It is another object of this invention to provide a method of treating aqueous systems to effectively inhibit corrosion of ferrous metals in contact with the aqueous system.

In accordance with the present invention, there have been provided certain novel naphthalene polycarboxylic acids having the formula:

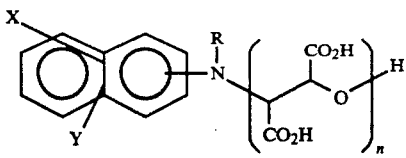

wherein X is —$CO_2H$ or —$SO_3H$, Y is H, $C_1$ $C_6$ alkyl, alkoxy, —$CO_2H$, or —$SO_3H$, R is H, $C_1$ to $C_6$ alkyl, COR' or $CO_2R'$, R' is alkyl and n is an integer from 1 to 20 or water soluble salts thereof which are useful in water treatment.

Also provided in accordance with the present invention, is a method of controlling the deposition of scale on surfaces in contact with an aqueous system which comprises adding to the system the above naphthalene polycarboxylic acids in an amount effective to inhibit scale formation.

Also provided in accordance with the present invention, is a method of controlling corrosion on surfaces in contact with an aqueous system which comprises adding to the system the above naphthalene polycarboxylic acids in an amount effective to inhibit corrosion.

DETAILED DESCRIPTION

The present invention is directed to certain novel naphthalene polycarboxylic acids and to a method of inhibiting the formation of scale in aqueous systems and to a method of inhibiting corrosion of ferrous based metals in contact with an aqueous system, which involves adding to the system naphthalene polycarboxylic acid as hereinafter described, in an amount effective to inhibit scale formation and/or to inhibit corrosion. The naphthalene polycarboxylic acids of the present invention can be represented by the following formula:

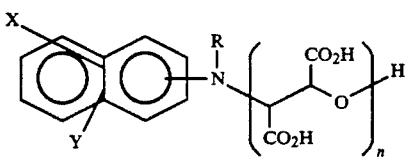

wherein X is —$CO_2H$ or —$SO_3H$, Y is H, $C_1$ to $C_6$ alkyl, alkoxy, —$CO_2H$ or —$SO_3H$, R is H, $C_1$ to $C_6$ alkyl, COR' or $CO_2R'$, R' is $C_1$ to $C_6$ alkyl and n is an integer from 1 to 20, and water soluble salts thereof. In a preferred embodiment, X is $SO_3H$, Y is H, —$CO_2H$ or —$SO_3H$ and R is H or —$CH_3$. The naphthalene polycarboxylic acids of this invention may also be used in the form of alkali metal salts and are usually in the form of the sodium salt. Other suitable water soluble salts include potassium, ammonium, lower amine salts, and the like. The free acids may also be used and all of the acidic hydrogens need not be replaced nor need the cation be the same for those replaced. Thus, the cation may be any one of or a mixture of $NH_4$, Na, K, etc. The naphthylamine polycarboxylic acids are readily converted into the water soluble salts by conventional methods.

The naphthylamine polycarboxylic acids of this invention, having the above formula wherein n is 1, may be prepared by reacting an epoxysuccinate or an admixture of an epoxysuccinate and a tartrate with a molar equivalent of an amine compound in an aqueous medium to form an alkali metal salt of an amino polycarboxylic acid. This procedure is more fully disclosed in U.S. Pat. No. 3,929,874 to Beerman et al, which is incorporated herein in its entirety. See also Y. Matsuzawa et al, Chemical Abstract 81. 77484m (1974), J. Oh-hashi et al, Chem. Soc Jap. 40, 2997 (1967) and H. Hauptmann et al, Chemical Abstracts 57, 16732g (1962) which are also incorporated herein by reference in their entirety.

The preparation of the naphthalene polycarboxylic acids of this invention having the above formula wherein n is from 2 to 20 is analagous to U.S. Pat. No. 4,654,159 which is incorporated herein in its entirety. In general, the naphthalene polycarboxylic acids are prepared by treating an epoxysuccinate or an admixture of an epoxysuccinate and a tartrate together with the n=1 compound from the above procedure with an alkaline calcium compound in an aqueous media to form the alkali metal and/or calcium salts of an ether hydroxypolycarboxylate and optionally separating the salts from the aqueous media.

In accordance with this invention, the formation of scale in an aqueous system, particularly calcium carbonate scale, may be inhibited by adding the naphthalene polycarboxylic acids of the above formula, wherein n is greater than 2, or their water soluble salts, to the aqueous system in an amount effective to either inhibit the formation of scale or to remove scale deposits which may already be present in the system. The precise dosage of the scale inhibiting agents of this invention depends to some extent on the nature of the aqueous system in which it is to be incorporated i.e., the amount of hardness causing and scale forming compounds present in the system, and the degree of protection desired, as well as the degree of scale which may be deposited in the system. The compositions of this invention are preferably added to the system in substoichiometric amounts to the scale forming salt and accordingly, are known to those skilled in the art as threshold inhibitors. Threshold inhibition describes the phenomenon whereby a sub-stoichiometric amount of a scale inhibitor can stabilize a solution from precipitation. Threshold inhibition generally takes place under conditions where a small amount i.e. 1 to 100 ppm of an additive will stabilize the solution which contains many orders of magnitude greater concentration of scale forming salts. Thus, in general, the amount of naphthalene polycarboxylic acid added to the system can be from about 0.1 ppm to 1000 ppm and is preferably 0.1 ppm to 100 ppm and is most preferably in the range of from 0.5 to 10 ppm. The exact dosage amount required with respect to a particular aqueous system can be readily determined in conventional manners which are known to those of ordinary skill in the art.

The naphthalene polycarboxylic acids of this invention have also been found to be effective for inhibiting corrosion of ferrous-based metals which are in contact with an aqueous system. Thus, in accordance with this aspect of the invention, corrosion of ferrous-based metals which are in contact with an aqueous system may be inhibited by adding to the system a naphthalene polycarboxylic acid having the above-described formula, wherein n is 1 or 2, in an amount effective to inhibit corrosion.

The scale inhibiting compositions of this invention are particularly suitable for use in aqueous systems having a high degree of hardness and have exhibited a high degree of insensitivity to relatively high concentrations of both magnesium and calcium. It is considered an important feature of this invention, that the claimed compositions be calcium insensitive. Calcium sensitivity refers to the tendency of a compound to precipitate with calcium ions in solution. The calcium insensitivity of the claimed compositions permits their use in aqueous systems having water with relatively high hardness. The test for calcium insensitivity of a compound, as used in this application, involves a cloud point test (hereinafter the CA500 cloud point test) where the compound is added to hard water containing 500 ppm calcium ion (as $CaCO_3$) which is buffered at pH 8.3 using 0.005 M borate buffer and which has a temperature of 60° C. The amount of compound which can be added to the solution until it becomes turbid (the cloud point) is considered to be an indicator of calcium insensitivity.

The calcium insensitive compounds of this invention have cloud points of at least about 25 ppm as determined by the CA500 cloud point test, and preferably have cloud points of at least about 40 ppm.

The aqueous systems which may be advantageously treated in accordance with the polymers of this invention include, but are not limited to cooling water systems such as e.g. cooling towers, desalinization units, gas scrubbers, as well as to boiler systems and other recirculating water systems where scale deposits are known to form.

The compounds of this invention may be used in combination with other water treatment components customarily employed in the aqueous system including, but not limited to other scale inhibitors, corrosion inhibitors, biocides, dispersing agents, antifoaming agents, oxygen scavengers, sequestering agents, and the like and mixtures thereof.

The scale inhibitors of this invention may be added to the system by any convenient mode, such as by first forming a concentrated aqueous solution of the naphthalene polycarboxylic acids or their water soluble salts, preferably containing between 1 and 50 total weight percent of the compound, and then feeding the concentrated aqueous solution to the aqueous system at some convenient point. In many instances the scale inhibitors may be added to the make-up or feedwater lines through which water enters the system. Typically, an injector calibrated to deliver a predetermined amount periodically or continuously to the makeup water is employed.

Without further elaboration, it is believed that one skilled in the art, using the preceding detailed description can utilize the present invention to its fullest extent.

The following examples are provided to illustrate the invention in accordance with the principles of this invention, but are not to be construed as limiting the invention in any way except as indicated in the appended claims. All parts and percentages are by weight unless otherwise indicated.

EXAMPLE 1

A solution of disodium epoxysuccinate (9.7g, 55 mmol) in 38 ml water was placed in a flask under a nitrogen atmosphere. 5-Amino-2-naphthalenesulfonic acid (11.2g, 50 mmol) and potassium hydroxide (3.4g, 61 mmol) were added to the solution. The pH of the resulting solution was adjusted to 9 by the addition of 0.4g 3N hydrochloric acid. The resulting mixture was heated to reflux for 23 hours. Examination of the reaction product by proton NMR showed it contained N-2-(6-sulfonaphthyl)hydroxyaspartic acid (ANS-HS) contaminated by a very minor amount of tartaric acid.

EXAMPLE 2

A solution of disodium epoxysuccinate (9.7g, 55 mmol) in 38 ml water was placed in a flask under a nitrogen atmosphere. 7-Amino-1,3-naphthalenedisulfonic acid monopotassium salt (17.1g, 50 mmol) and potassium hydroxide (3.2g, 57 mmol) were added. After adjusting the pH of the solution to 9 with 0.5g 3N hydrochloric acid, it was heated to reflux for 24 hours. Examination of the reaction product by proton NMR showed that it contained N-2-(6,8-disulfonaphthyl)-hydroxyaspartic acid (ANDS-HS) contaminated by a minor amount of tartaric acid.

EXAMPLE 3

N-2-(6,8-disulfonaphthyl)-hydroxyaspartic- acid (1.0 mmol) was reacted with disodium epoxysuccinate (17.6g, 100 mmol) by heating these two reactants together with calcium hydroxide (1.1g, 15 mmol) in 27 ml water for 17 hours at 60–65° C. and then for 5 hours at about 75° C. During this time the reaction was kept under a nitrogen atmosphere. Examination of the product by proton and carbon NMR showed that the desired product had been formed. The average value of "n" of the polyepoxysuccinate portion of the product (as illustrated below) was determined by carbon NMR to be 9.8.

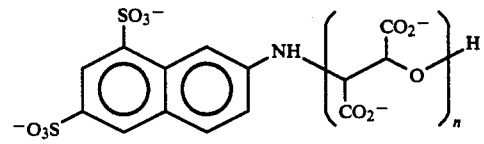

EXAMPLE 4

N-2-(6,8-disulfonaphthyl)-hydroxyaspartic acid (5.0 mmol) was reacted with disodium epoxysuccinate (17.6g, 100 mmol) by heating these two reactants together with calcium hydroxide (1.1g, 15 mmol) in 27 ml water for 16 hours at 56–58° C. and then for 5 hours at about 70–75° C. During this time the reaction was kept under a nitrogen atmosphere. Examination of the product by proton and carbon NMR showed that the desired product had been formed. The average value of "n" of the polyepoxysuccinate portion of the product (as illustrated below) was determined by carbon NMR to be 5.2.

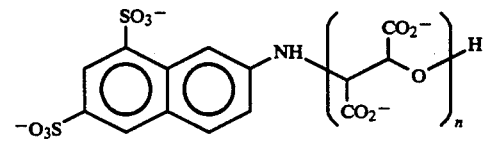

EXAMPLE 5

Two representative compounds of this invention were evaluated for their effectiveness in inhibiting corrosion in aqueous systems using an Aerated Solution Bottle test according to the following procedure and used a standard corrosive water having the following composition:

| Standard Corrosive Water |
| --- |
| 12.8 mg/l CaCl$_2$ |
| 110.7 mg/l CaSO$_4$—2H$_2$O |
| 54.6 mg/l MgSO$_4$ |
| 75.7 mg/l NaHCO$_3$ |

Mild steel coupons (4.5 in. ×0.5 in.) were immersed in 15% hydrochloric acid for 15 minutes, then rinsed sequentially in saturated sodium bicarbonate solution, distilled water and isopropanol, dried and stored in a desiccator. They were weighed prior to use in the corrosion test.

The desired amount or corrosion inhibitor was dissolved in 850 ml of the standard corrosive water listed above. The solution was heated in a thermostatted bath at 55° C. After the temperature had equilibrated the pH of the solution was adjusted to 8.5. Two coupons were suspended in the solution and air was passed into the solution at 250 ml/min. After 48 hours, the coupons were removed and cleaned with steel wool, rinsed, dried, and weighed again. The rate of corrosion was calculated from the weight loss and was expressed in mils per year (mpy). The results are shown in the following table.

TABLE 1

| | Dosage ppm | Corrosion Rate (mpy) |
| --- | --- | --- |
| Blank | — | 70 |
| ANS-HS | 200 | 3.0 |
| | 100 | 46 |
| ANDS-HS | 200 | 2.9 |
| | 100 | 48 |
| *AHNS-HS | 250 | — |
| | 200 | 32 |
| | 150 | 44 |

*N-2-(5-hydroxy-7-sulfonaphthyl)-hydroxy aspartic acid.

EXAMPLE 6

Calcium sensitivity test determines the tendency of a chemical to precipitate with calcium ions in solution.

Calcium insensitivity is considered an important feature of this invention because it allows the compound of this invention to be used effectively in water of relatively high hardness. The test for calcium insensitivity of a compound as used in this application involves a cloud point test where the compound is added to a hard water containing 500 ppm calcium ion (as CaCO$_3$) which is buffered at pH 8.3 using 0.005 M borate buffer and has a temperature of 60° C. The amount of compound which can be added until the solution becomes turbid (the cloud point) is considered to be an indicator of calcium sensitivity. The calcium insensitive compounds of this invention have cloud points of at least about 25 ppm as determined by this specific test.

Formation of the co-precipitates of calcium with polyacrylic acid, polymethacrylic acid and polymaleic acid were at cloud points of 4 ppm, 6 ppm, and 12 ppm, respectively. This result indicated that polyacrylic acid, polymethacrylic acid and polymaleic acid were very sensitive to calcium hardness and prone to form calcium polymer precipitates at low treatment concentrations. In contrast, the naphthalene polycarboxylic acids, as illustrated in Table 1, were relatively insensitive to calcium with cloud points at 40 and 77 ppm, respectively.

TABLE 2

| Treatment | Calcium Sensitivity Cloud Point (ppm) |
| --- | --- |
| Polyacrylic Acid | 4 |
| Polymethacrylic Acid | 6 |
| Polymaleic Acid | 12 |
| Product of Example 3 | 40 |
| Product of Example 4 | 77 |

EXAMPLE 7

Threshold inhibition test measures the ability of a chemical to inhibit calcium carbonate formation.

Laboratory tests for calcium carbonate threshold inhibitors were performed under the following water conditions: water containing 283 ppm Ca$^{+2}$, 184 ppm Mg$^{+2}$ and 423 ppm HCO$_3^-$ (all as CaCO$_3$). The test solution was prepared in a 1000 ml beaker and 5 ppm of the additive being tested was added to the above water. The final volume of the solution was made up to 800 ml. The solution was stirred with a magnetic stir bar and heated by a stainless steel immersion heater to 130° F. The pH of the solution was monitored and adjusted at pH 7.15 with the addition of dilute HCl. On achieving the required temperature, 0.1 N NaOH was added at a rate of 0.32 ml/minute using a syringe pump.

The pH was monitored and recorded during the titration. A decrease or plateau in pH reading is observed when calcium carbonate starts to precipitate. This point is termed the critical pH (pH$_c$). An effective threshold inhibitor will raise the critical pH, compared to the blank, and require more base (hydroxide) to reach pH$_c$. Results are summarized in Table 3.

As shown in Table 3, naphthalene polycarboxylic acid is an effective calcium carbonate threshold inhibitor. Also apparent from the data in Table 3 is the general unpredictability of the effectiveness of similar additives for threshold inhibition when viewed on the basis of chemical structure alone. Clearly the effectiveness of the compositions of this invention in providing calcium carbonate threshold inhibition was comparable to polymaleic acid and polyacrylic acid and yet the results were far superior to polymethacrylic acid which is structurally similar to these compounds.

TABLE 3

| | Threshold Inhibition | |
| --- | --- | --- |
| Additive | Critical pH pH$_c$ | Meq. OH$^-$/Liter to pH$_c$ |
| Blank | 8.12 | 0.91 |
| Polymaleic Acid | 9.12 | 2.79 |
| Polyacrylic Acid | 9.33 | 3.62 |
| Polymethacrylic Acid | 8.93 | 1.78 |
| Product of Example 3 | 9.32 | 3.33 |
| Product of Example 4 | 9.19 | 2.78 |

We claim:

1. A scale and/or corrosion inhibitor composition useful for treating aqueous systems which loose water upon evaporation comprising a naphthylamine polycarboxylic acid having the formula:

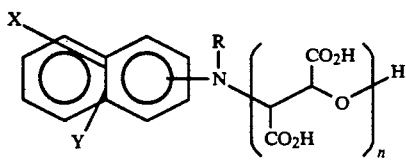

wherein X is CO₂H or SO₃H, Y is H, $C_1$ to $C_6$ alkyl, CO₂H or SO₃H, R is H, $C_1$ to $C_6$ alkyl, CO₂R' or COR', R' is $C_1$ to $C_6$ alkyl, n is an integer from 1 to 20, and water soluble salts thereof.

2. A composition according to claim 1 wherein X is, SO₃H and n is 1.

3. A composition according to claim 1 wherein X is —SO₃H, Y is H, —CO₂H or —SO₃H, and R is H or —CH₃.

4. A composition according to claim 2 wherein the naphthylamine polycarboxylic acid has the formula:

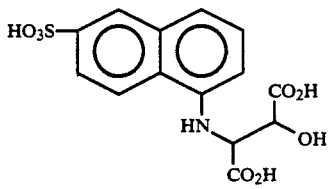

5. A composition according to claim 2 wherein Y is

6. A method according to claim 5 wherein the naphthylamine polycarboxylic acid has the formula:

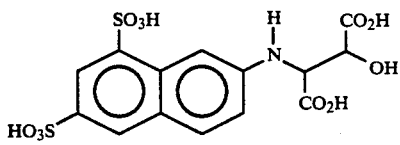

7. A composition according to claim 5 wherein the naphthylamine polycarboxylic acid has the formula:

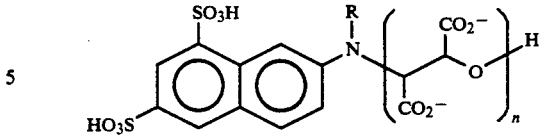

wherein n is an integer from 2 to 20 and R is H.

8. A composition according to claim 7 wherein n is an integer from 4 to 12.

9. A method for inhibiting or preventing the formation of scale on surfaces in contact with an aqueous systems which looses water upon evaporation comprising adding to the system the composition of claim 1 wherein n is greater than 2 in an amount effective to inhibit scale formation.

10. A method for inhibiting or preventing corrosion of ferrous-based metals in contact with an aqueous systems comprising adding to the system the composition of claim 1 wherein n is 1 or 2 in an amount effective to inhibit or prevent the formation of corrosion.

11. A method according to claim 9 wherein n is from 4 to 12.

12. A method according to claim 9 wherein the effective amount is in the range of from 0.1 to 1000 ppm.

13. A method according to claim 9 wherein the effective amount is in the range of from 0.1 to 100 ppm.

14. A method according to claim 9 wherein X is —SO₃H, Y is H, —CO₂H or —SO₃H and R is H or —CH₃.

15. A method according to claim 10 wherein the effective amount is in the range of from 0.1 to 1000 ppm.

16. A method according to claim 10 wherein the effective amount is in the range of from 0.1 to 100 ppm.

17. A method according to claim 10 wherein X is —SO₃H, Y is H, —CO₂H or —SO₃H and R is H or —CH₃.

18. A method for inhibiting or preventing corrosion in aqueous systems comprising adding to the system the composition of claim 4.

19. A method for inhibiting or preventing corrosion in aqueous systems comprising adding to the system the composition of claim 6.

20. A method for inhibiting or preventing the formation of scale in aqueous systems comprising adding to the system the composition of claim 7.

* * * * *